US009241744B2

(12) United States Patent
Blake et al.

(10) Patent No.: US 9,241,744 B2
(45) Date of Patent: Jan. 26, 2016

(54) TARGETING ASSEMBLY FOR A COMPRESSION NAIL SYSTEM

(75) Inventors: Stephen Blake, Allen, TX (US); Miguel Franco, Addison, TX (US); Dimitri Protopsaltis, Memphis, TN (US); Michael Thomas, Van Alstyne, TX (US)

(73) Assignee: AMEI TECHNOLOGIES, INC., Wilmington, DE (US)

( * ) Notice: Subject to any disclaimer, the term of this patent is extended or adjusted under 35 U.S.C. 154(b) by 452 days.

(21) Appl. No.: 13/586,619

(22) Filed: Aug. 15, 2012

(65) Prior Publication Data
US 2013/0046311 A1 Feb. 21, 2013

Related U.S. Application Data (60) Provisional application No. 61/523,814, filed on Aug. 15, 2011.

(51) Int. Cl.
*A61B 17/72* (2006.01)
*A61B 17/17* (2006.01)

(52) U.S. Cl.
CPC ......... *A61B 17/7225* (2013.01); *A61B 17/1725* (2013.01)

(58) Field of Classification Search
None
See application file for complete search history.

(56) References Cited

U.S. PATENT DOCUMENTS

| 6,033,407 | A  | * | 3/2000 | Behrens ........................ 606/62 |
| 2005/0245934 | A1 | | 11/2005 | Tuke et al. |
| 2008/0221577 | A1 | * | 9/2008 | Elghazaly ..................... 606/64 |
| 2009/0093813 | A1 | | 4/2009 | Elghazaly |
| 2009/0099571 | A1 | | 4/2009 | Cresina et al. |
| 2009/0234369 | A1 | | 9/2009 | Bax et al. |
| 2009/0299375 | A1 | | 12/2009 | Wack et al. |
| 2012/0109217 | A1 | * | 5/2012 | Perineau ............ A61B 17/1725 606/301 |
| 2012/0226326 | A1 | * | 9/2012 | Overes et al. ................ 606/329 |

OTHER PUBLICATIONS

International Search Report and Written Opinion, PCT/US2012/050982, dated May 15, 2013, 9 pages.

* cited by examiner

*Primary Examiner* — Samuel Hanna
(74) *Attorney, Agent, or Firm* — Baker & McKenzie LLP (57) ABSTRACT

Targeting assemblies for implanting a compression nail are disclosed. An exemplary targeting assembly may include first and second arms coupled by a connecting shaft. The first and second arms may either or both be operable to rotate about a longitudinal axis defined by the connecting shaft. In some embodiments, the use of the disclosed targeting assembly allows for reduced misalignment of the alignment holes in the arms during the implant process.

15 Claims, 12 Drawing Sheets

TARGETING ASSEMBLY FOR A COMPRESSION NAIL SYSTEM

PRIORITY OF THE APPLICATION

This application claims priority to U.S. Provisional Patent Application No. 61/523,814, filed Aug. 15, 2011, the entirety of which is hereby incorporated by reference.

FIELD OF THE INVENTION

The disclosed embodiments relate generally to medical device technology, and more specifically to a targeting assembly for a compression nail system.

BACKGROUND OF THE INVENTION

Compression nail systems have been used in a number of medical applications, including arthrodesis of joints. Arthrodesis is a procedure to fuse the bones that form a joint, such as an ankle. Arthritis, deformity, fracture, or other trauma affecting the joint or other bones may be treated with an arthrodesis procedure. To fuse the joints, pins, plates, screws, wires, or rods may be implanted in the bones to compress them together until they fuse.

BRIEF SUMMARY

Disclosed herein is a targeting assembly comprising a connecting shaft defining a longitudinal axis. The targeting assembly may also include a first arm having a proximal portion and a base portion, the base portion of the first arm being connected to the connecting shaft, and the first arm. The targeting assembly may further include a second arm having a proximal portion and a base portion, the base portion of the second arm being rotatably coupled to the connecting shaft, and the proximal portion of the second arm being operable to rotate about the longitudinal axis. In an embodiment, the first arm comprises at least one alignment hole defined through the proximal portion of the first arm, and the second arm comprises at least one alignment hole defined through the proximal portion of the second arm.

Also disclosed herein is a nail compression system comprising a connecting shaft defining a longitudinal axis. The disclosed nail compression system may include a first arm having a proximal portion and a base portion, the base portion of the first arm being connected to the connecting shaft, and a second arm having a proximal portion and a base portion, the base portion of the second arm being rotatably coupled to the connecting shaft, and the proximal portion of the second arm being operable to rotate about the longitudinal axis. The disclosed nail compression system may also include a compression element threadably coupled to the connecting shaft and a cup adjacent to the compression element, wherein the connecting shaft is disposed through a central opening of the cup, and wherein a rotation of the compression element is operable to translate the cup along the longitudinal axis. Moreover, the disclosed nail compression system may include a nail seated on an end portion of the connecting shaft, wherein the nail is aligned substantially along the longitudinal axis. In an embodiment, the first arm comprises at least one alignment hole defined through the proximal portion of the first arm, and the second arm comprises at least one alignment hole defined through the proximal portion of the second arm.

Further disclosed herein is an exemplary embodiment of a method of implanting a compression nail. The exemplary method may include providing a nail compression system that comprises: 1) a connecting shaft defining a longitudinal axis; 2) a first arm having a proximal portion and a base portion, the base portion of the first arm being connected to the connecting shaft, and the first arm; and 3) a second arm having a proximal portion and a base portion, the base portion of the second arm being rotatably coupled to the connecting shaft, and the proximal portion of the second arm being operable to rotate about the longitudinal axis. The nail compression system may further include a nail seated on an end portion of the connecting shaft, wherein the nail is aligned substantially along the longitudinal axis and comprises a plurality of screw holes defined therethrough, wherein when the second arm is in a first rotational position, a first screw of the nail is in lateral alignment with a first alignment hole defined through the proximal portion of the second arm. The exemplary embodiment may further include inserting the nail, rotating the second arm to the first rotational position, inserting, with the second arm in the first rotational position, a first fastener through the first alignment hole of the second arm into the first screw hole, and inserting a second fastener through an alignment hole defined in the proximal portion the first arm into a second screw hole of the nail.

BRIEF DESCRIPTION OF THE DRAWINGS

Embodiments are illustrated by way of example in the accompanying figures, in which like reference numbers indicate similar parts, and in which.

DETAILED DESCRIPTION

Figure 1:
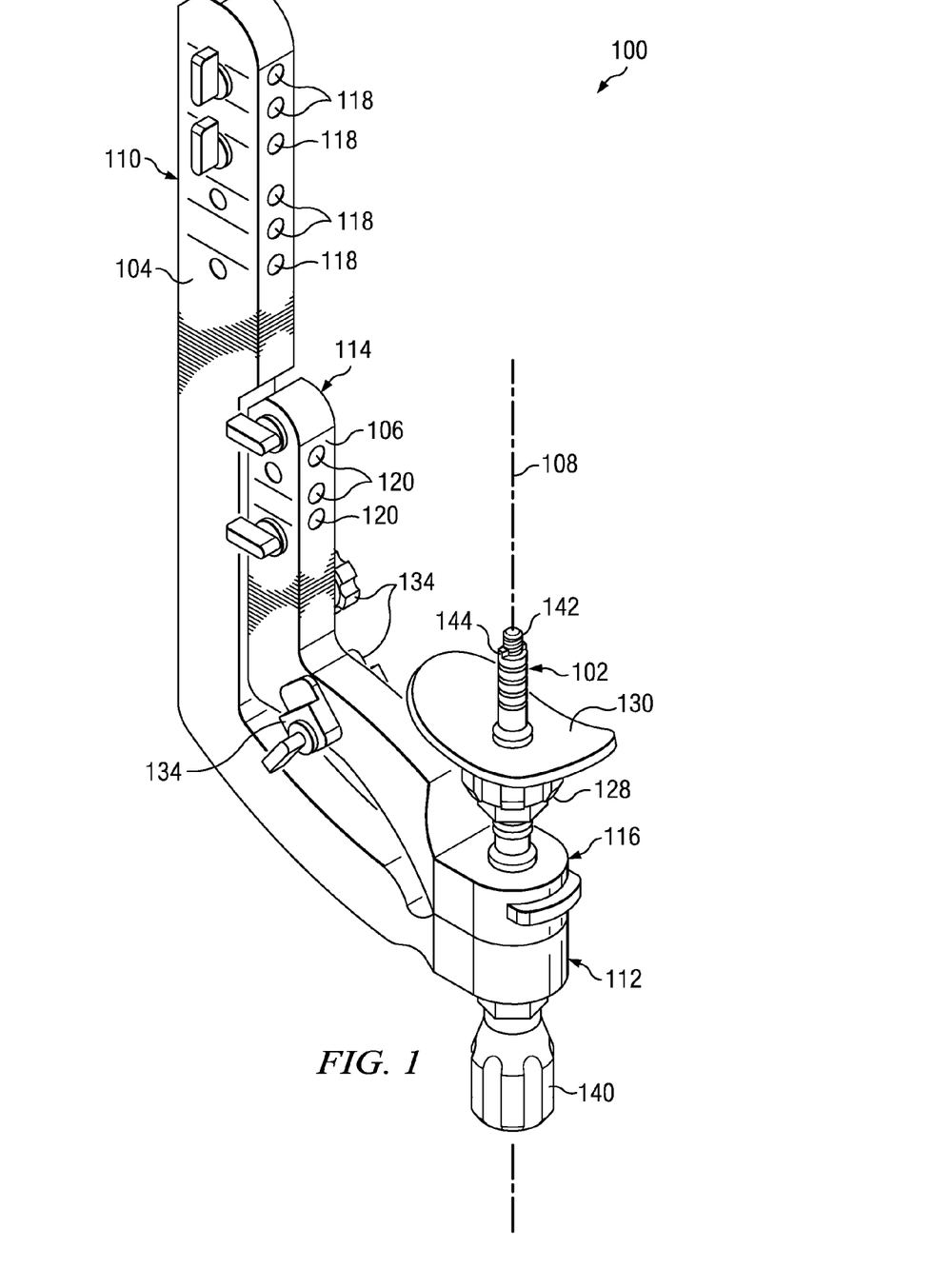
FIG. 1 is an elevational view of an exemplary embodiment of a targeting assembly having a rotating arm in a first rotational position, in accordance with the present disclosure.

FIG. 1 shows an exemplary embodiment of a targeting assembly 100 that may be used for the implantation of a compression nail in an ankle or other suitable human tissues. The targeting assembly 100 may include a connecting shaft 102 for connecting a first arm 104 and a second arm 106. In an embodiment, the first and second arms 104 and 106 may be made of a radio-translucent material. The first arm 104 may include a proximal portion 110 and a base portion 112, in which the base portion 112 of the first arm 104 is connected to the connecting shaft 102. In an exemplary embodiment, the first arm 104 and the connecting shaft 102 may be rotationally fixed relative to each other to provide improved stability. In another exemplary embodiment, the first arm 104 may be rotatably coupled to the connecting shaft 102 and thus operable to rotate about the connecting shaft 102. The second arm 106 may include a proximal portion 114 and a base portion 116, in which the base portion 114 of the second arm 106 is rotatably coupled to the connecting shaft 102. In an exemplary embodiment, the proximal portion 114 of the second arm 106 may be operable to rotate about a longitudinal axis 108 defined by the connecting shaft 102. For example, the second arm 106 may rotate from a first rotational position as shown in FIG. 1 to a second rotational position separated by a predetermined angular displacement.

Figure 2:
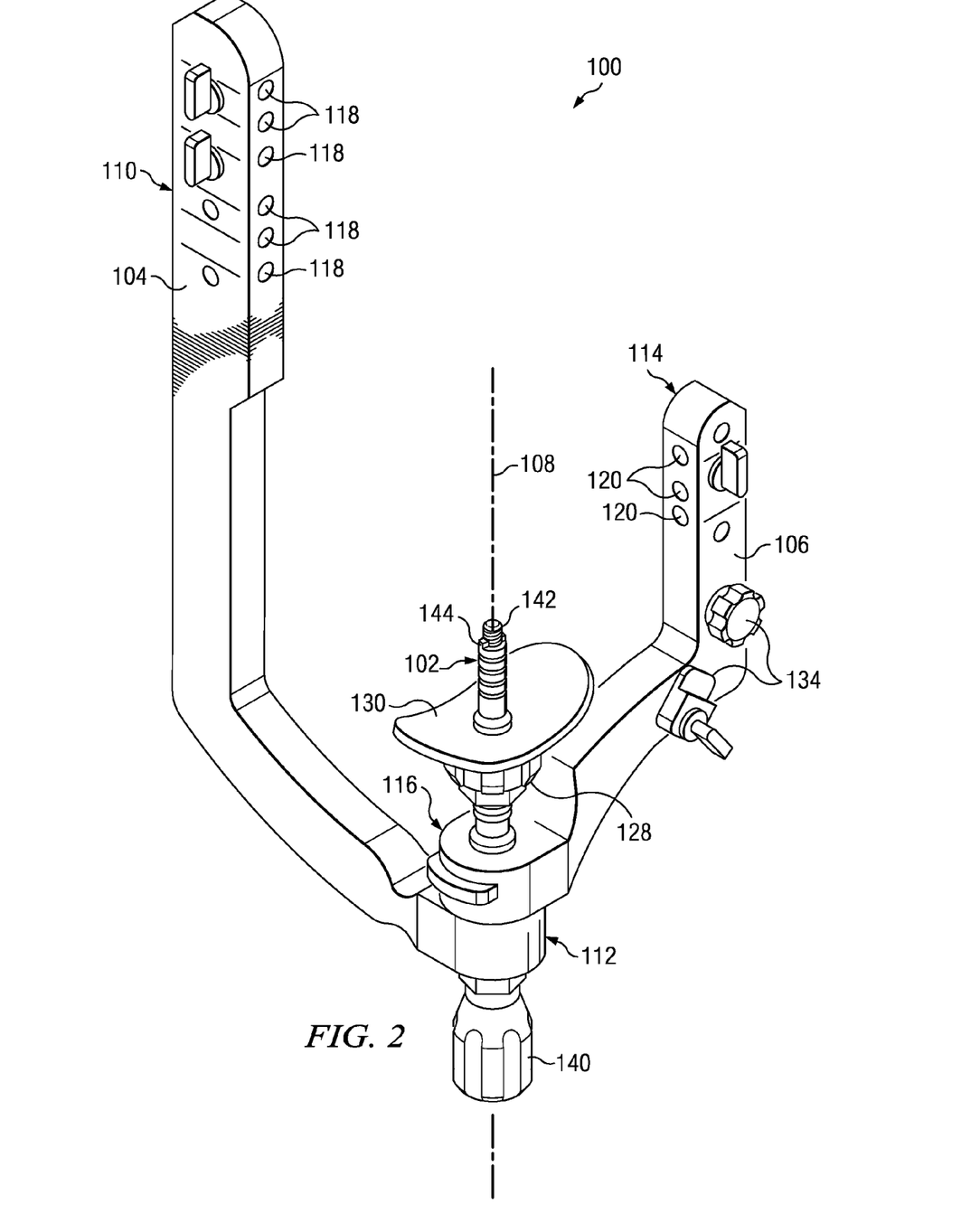
FIG. 2 is an elevational view of the targeting assembly shown in FIG. 1 having the rotating arm in a second rotational position, in accordance with the present disclosure.

FIG. 2 shows an exemplary embodiment of the targeting assembly 100, with the second arm 106 rotated to an exemplary second rotational position. In the embodiments illustrated in FIGS. 1 and 2, the first and second rotational positions have an angular displacement of 90 degrees. In other embodiments, the second arm 106 may be rotated to any rotation position as needed to allow the desired approach to insert a screw. In an exemplary embodiment, the second arm 106 is operable to rotate about the longitudinal axis 108 in increments of predetermined angular displacements, such as 30, 45, 60, 90, or 180 degrees. One of ordinary skill in the art would appreciate that the increments need not be the same, and the amount of predetermined angular displacement for each increment may be customized to satisfy the operative preferences of the surgeon.

Referring to FIGS. 1-2, the first arm 104 may include at least one alignment hole 118 defined through the proximal portion 110 of the first arm 104, and the second arm 106 may include at least one alignment hole 120 defined through the proximal portion 114 of the second arm 106. The alignment holes 118 and 120 allow a surgeon to target, drill, and insert screws through the bone and into a compression nail (not shown) in the desired orientation, which will be discussed in greater details below. In the illustrated embodiments, each of the first arm 104 and second arm 106 includes a plurality of alignment holes 118 and 120, respectively. In other embodiments, the first and second arms 104 and 106 may be configured to have the same or different number of alignment holes 118 and 120, respectively, which can be one, two, three, four, five, or greater, depending the surgical needs and the number of options desired or the relative geometry of any associated implant.

Figure 3:
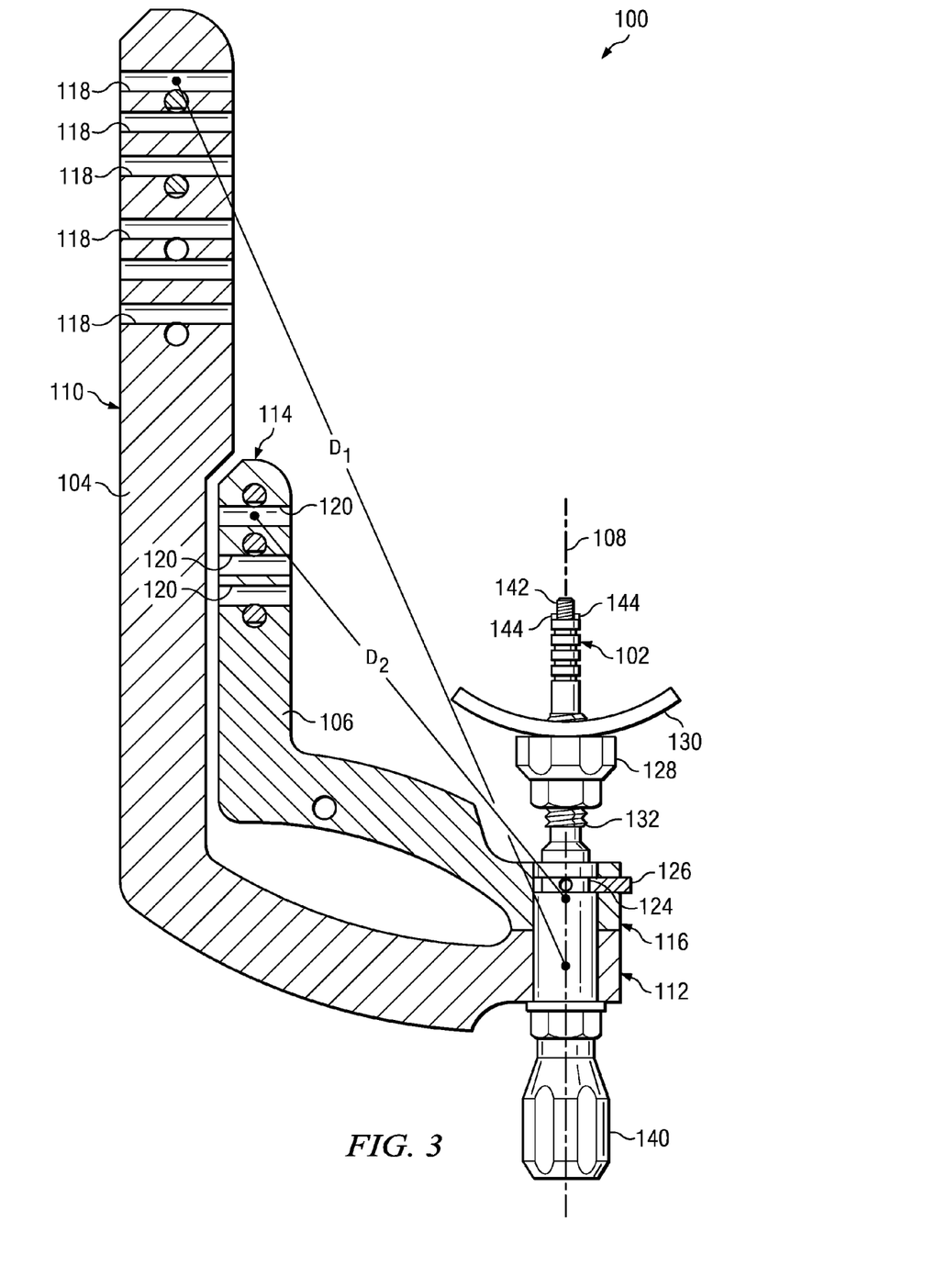
FIG. 3 is a cross-sectional view of the targeting assembly shown in FIG. 1.

FIG. 3 is a cross-sectional view of the targeting assembly 100 illustrating a distance $D_1$ between one alignment hole 118 of the first arm 104 and the base portion 112 of the first arm 104. Also illustrated in FIG. 3 is a distance $D_2$ between one alignment hole 120 of the second arm 106 and the base portion 116 of the second arm 106. In an exemplary embodiment in which the first arm 104 is rotationally fixed relative to the connecting shaft 102, $D_1$ may be configured to be greater than $D_2$ to reduce any misalignment of the alignment hole 120 due to the rotation of the second arm 106. It is to be appreciated that the farther away the alignment hole 120 is disposed from a point of rotation, the larger magnification of any misalignment would be resulted. As such it is desirable to configure the rotating second arm 106 to have a smaller $D_2$ than the $D_1$ of the fixed first arm 104. It is to be appreciated that the endpoints of $D_1$ and $D_2$ may be defined in a number of ways. In the illustrated embodiment, the endpoints of $D_1$ are the center of an alignment hole 118 and a point along the longitudinal axis 108 within the base portion 112. In an embodiment, an endpoint along the longitudinal 108 axis may approximate a center of rotation of the first arm 104 or second arm 106. In another embodiment, endpoints of $D_1$ and $D_2$ may be proximate to the alignment holes 118 and 120 and the longitudinal axis 108.

Figure 4:
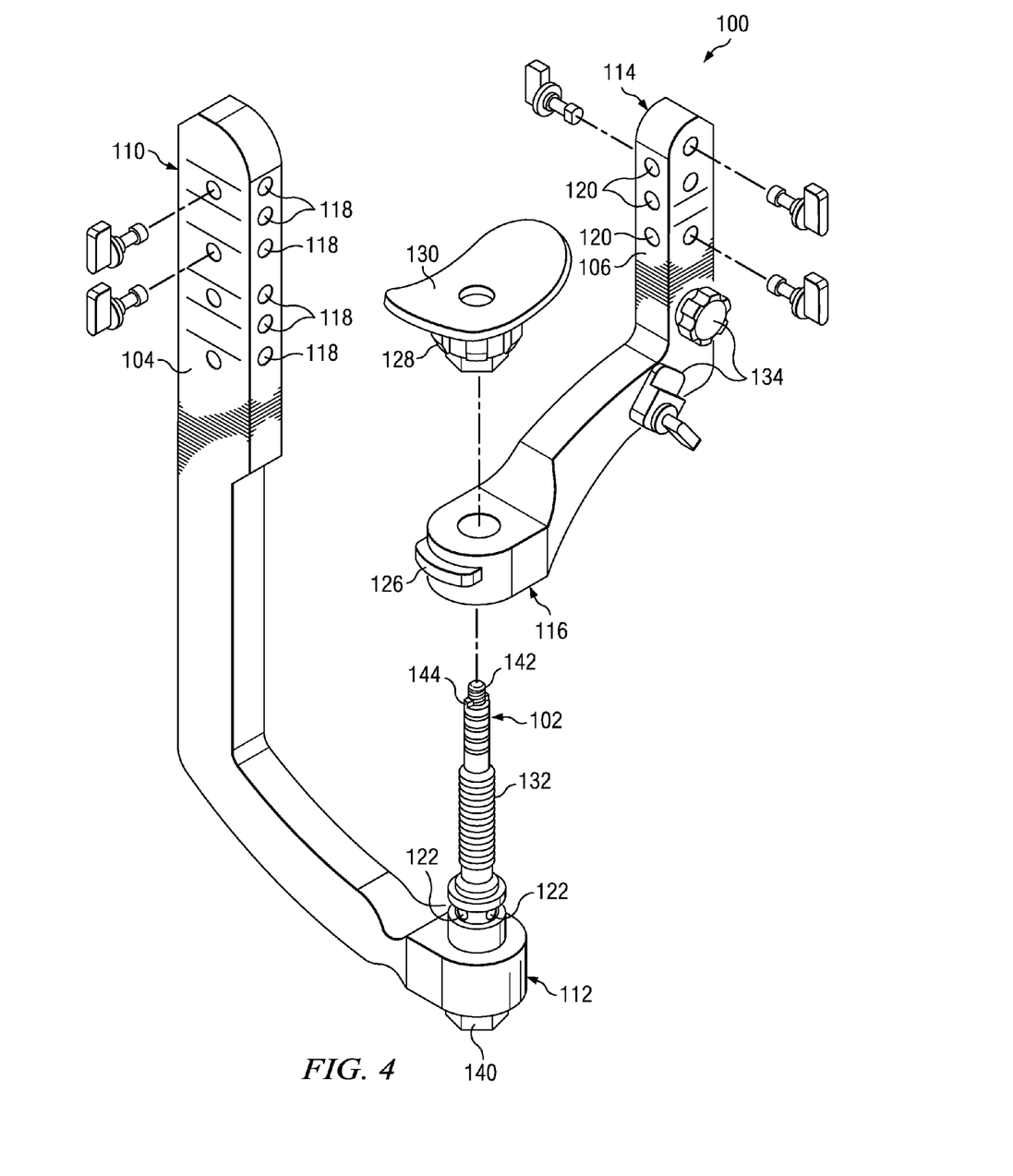
FIG. 4 is an exploded view of the targeting assembly shown in FIG. 1.

FIG. 4 is an exploded view of the targeting assembly 100 showing exemplary mechanisms for connecting the first and second arms 104 and 106 to the connecting shaft 102. As one of ordinary skill in the art may appreciate from FIG. 4, various mechanisms may be used to connect the first arm 104 to the connecting shaft 102. In an embodiment, the connecting shaft 102 and the first arm 104 may be modular components that are releasably coupled using any suitable coupling mechanisms known in the art. In another embodiment, the connecting shaft 102 and the first arm 104 may be preassembled or integrally formed into one part.

The connecting shaft 102 and the second arm 106 may also releasably coupled using any suitable coupling mechanisms known in the art. As shown in the exemplary embodiment disclosed in FIGS. 3 and 4, one suitable mechanism is a latch mechanism. For example, the connecting shaft 102 may include a latch 124 and a plurality of recessed areas 122 defined in a circumferential surface of the connecting shaft 102. The latch 124 is operable to be received in one of the plurality of recessed areas 122 and engage the base portion 116 of the second arm 106, thereby keeping the second arm 106 in one rotational position about the longitudinal axis 108. In an embodiment, the plurality of recessed areas 122 may be spaced apart circumferentially by predetermined angular displacements, and the second arm 106 may rotate about the longitudinal axis 108 in increments substantially equal to the predetermined angular displacements. For example, the latch 124 may be released from the recessed area 122 to rotate the second arm 106 until a predetermined angular displacement is reached, at which point the latch 124 would be received in another recessed area 122 and seating the second arm 106 in a new rotational position. In an embodiment, the latch 124 may be mechanically coupled to or a part of a manual switch 126 such that a surgeon may use the switch 126 to remove the latch 124 from recessed areas 122 and allow a rotation of the second arm 106. For example, the latch 124 may be a spring-load pin removable by pressing on a switch 126. As discussed above, various increments of predetermined angular displacements may be used, such as 30, 45, 60, 90, or 180 degrees. One of ordinary skill in the art would appreciate that the increments need not be the same, and the amount of predetermined angular displacement for each increment may be customized to satisfy the operative preferences of the surgeon.

Referring to FIGS. 1-4, some embodiments of the targeting assembly 100 may further include a compression element 128 and a cup 130 adjacent to the compression element 128. The compression element 128 may be threadably coupled to the connecting shaft 102, and the connecting shaft 102 may be disposed through a central opening of the cup 130. The compression element 128 may comprise an internally threaded surface operable to mate with an externally threaded portion 132 of the connecting shaft 102. As such, a rotation of the compression element 128 would translate the cup 130 along the longitudinal axis 108. The illustrated compression element 128 may be desirable in some embodiments due to its ease of adjustment, but in other embodiments, other types of compression elements may be used to translate the cup 130.

Some embodiments of the targeting assembly 100 may further include a rod 140, and the connecting shaft 102 may have a central bore that receives the rod 140 therein. The rod 140 may include a tip 142 that extends upwardly outside of a top opening of the connecting shaft 102 and adjacent to a plurality of tabs 144 disposed on an end portion of the connecting shaft 102. The tip 142 may be threaded to engage complementary threads of an end portion of a nail (not shown) and rotate the nail to lock against the tabs 144.

In some embodiment, the second arm 106 may further include an angular adjustment mechanism 134 operable to secure an oblique aiming guide (not shown) along an oblique axis (not shown) that is offset from the longitudinal axis 108. As such, a screw (not shown) may be inserted at an oblique orientation while not being targeted at a nail (not shown), which will be further discussed below.

The use of the targeting assembly may allow for a number of advantages, which will be discussed with reference to an exemplary embodiment of a compression nail system 200 shown in FIG. 5. The compression nail system 200 includes a targeting assembly 201, which is substantially similar to the targeting assembly 100 shown in FIGS. 1-4. The targeting assembly 201 includes a connecting shaft 202 for connecting a first arm 204 and a second arm 206, and each of first arm 204 and second arm 206 may include a plurality of alignment holes 218 and 220, respectively. The first arm 204 may include a proximal portion 210 and a base portion 212, which is connected to the connecting shaft 202. In an embodiment, the first arm 204 and the connecting shaft 202 may be rotationally fixed relative to each other. In another exemplary embodiment, the first arm 204 may be rotatably coupled to the connecting shaft 102 and thus operable to rotate about the connecting shaft 202. The second arm 206 may include a proximal portion 214 and a base portion 216, which is rotatably coupled to the connecting shaft 202. In an embodiment, the proximal portion 214 of the second arm 206 may be operable to rotate about a longitudinal axis 208 defined by the connecting shaft 202. In an exemplary embodiment, the second arm 206 is operable to rotate about the longitudinal axis 208 in increments of predetermined angular displacements, such as 30, 45, 60, 90, or 180 degrees. The second arm 206 may be releasably coupled to the connector shaft 202 according the principles disclosed in the present disclosure to allow for incremental rotation of the second arm 206.

Similar to the targeting assembly 100, the targeting assembly 201 may further include a compression element 228 and a cup 230 adjacent to the compression element 228. The compression element 228 may be threadably coupled to the connecting shaft 202, and the connecting shaft 202 may be disposed through a central opening of the cup 230. As such, a rotation of the compression element is 228 would translate the cup 230 along the longitudinal axis 208. In an embodiment, the compression element 228 may comprise an internally threaded surface operable to mate with an externally threaded portion 232 of the connecting shaft 202.

Figure 5:
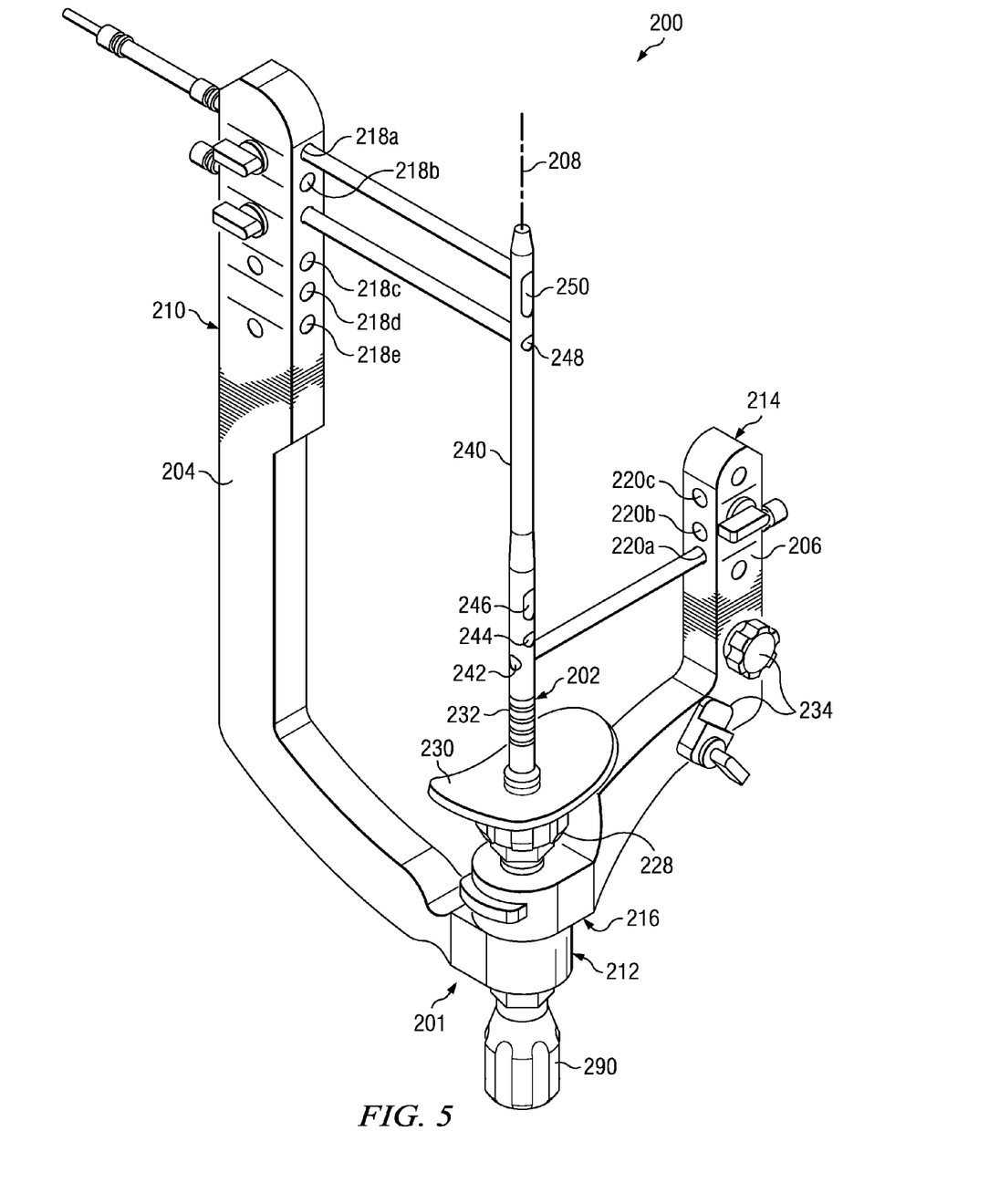
FIG. 5 is an elevational view of an exemplary embodiment of a compression system in accordance with the present disclosure.
Figure 6:
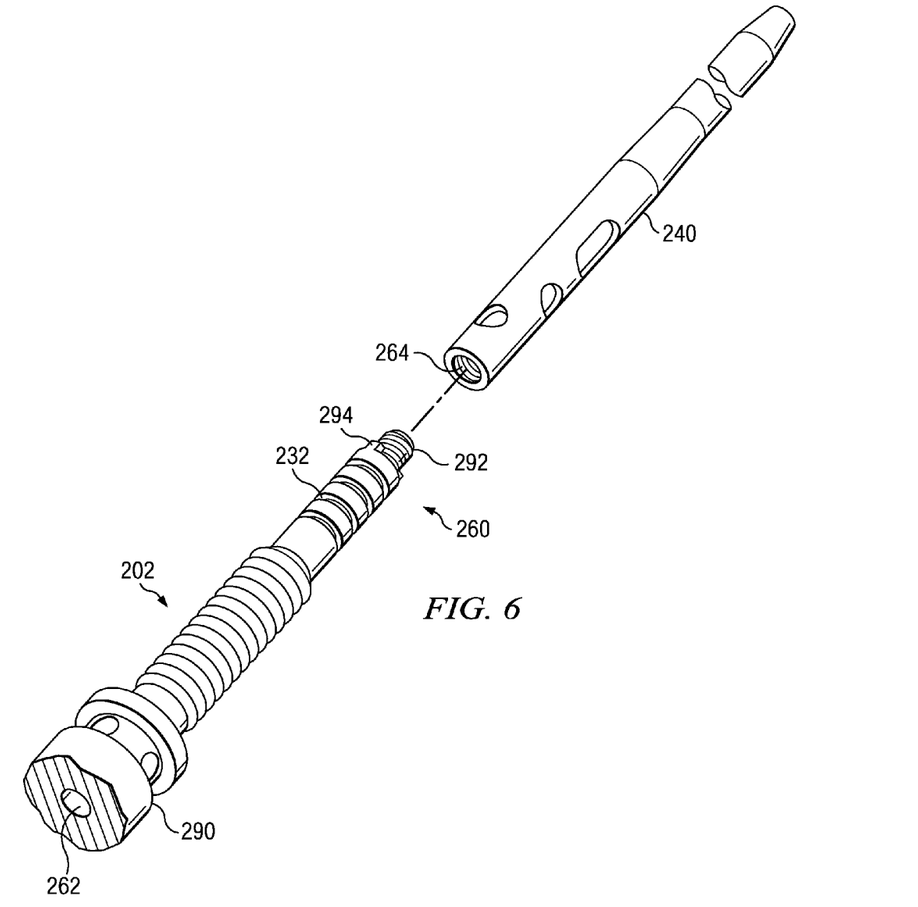
FIG. 6 is a cross-sectional view of a compression nail seated on a connector shaft of the compression system in FIG. 5.

Referring now to FIG. 5 and FIG. 6, in addition to the targeting assembly 201, the compression nail system 200 may also include a nail 240 seated proximate an end portion of the connecting shaft 202. In an embodiment, the targeting assembly 201 may include a rod 290, and the connecting shaft 202 may have a central bore that receives the rod 290 therein. The rod 290 may include a tip 292 that extends upwardly outside of a top opening of the connecting shaft 202 and adjacent to a plurality of tabs 294 disposed on an end portion of the connecting shaft 202. The tip 292 may be threaded to engage complementary threads of an end portion of the nail 240. A rotation of the rod 290 would rotate the nail 240 to lock it against the tabs 294. As such, the nail 240 may be aligned substantially along the longitudinal axis 208.

When the nail 240 is seated on the end portion 260 of the connecting shaft 202, a longitudinal aperture 262 of the rod 290 may meet an internal aperture 264 of the nail 240. As such, the internal aperture 264 of the nail 240 is accessible from the exterior of the targeting assembly 201 through the longitudinal aperture 262 of the rod 290.

Turning back to FIG. 5, in an embodiment, the nail 240 may include a plurality of screw holes 242, 244, 246, 248, and 250 defined therethrough. In an embodiment, first and second screw holes 242 and 244 may each define a lateral axis (not shown) orthogonal to the longitudinal axis. In an embodiment, the first and second screw holes 242 and 244 may define lateral axes (not shown) that are orthogonal to each other. The first screw hole 242 may be oriented such that it would be in lateral alignment with a first alignment hole 220a when the second arm 206 is in a first rotational position. The second screw hole 244 may be oriented such that it would be in lateral alignment with a second alignment hole 220b when the second arm 206 is in a second rotational position. In an embodiment, the first rotational position may be the rotational position of the second arm 206 as shown in FIG. 5, in which the second arm 206 is angularly displaced from the rotational position of the first arm 204 by approximately 90 degrees. In an embodiment, the second arm 206 may be rotated to a second rotational position where it would be angularly displaced from the rotational position of the first arm 204 by approximately 180 degrees. The angular displacements of 90 and 180 degrees for the first and second rotational positions, respectively, are merely exemplary embodiments, and one of ordinary skill in the art would appreciate from the present disclosure that the first and second rotational positions of the second arm 206 may be a variety of angular displacements from the first arm 204. Depending on the orientations of the first and second screw holes 242 and 244 of the nail 240, the first and second rotational positions of the second arm 206 may be adjusted accordingly.

The nail 240 may be any compression nail known in the art, including nails for ankle arthrodesis or other orthopedic procedures requiring compression of one or more bones. It is to be appreciated that a nail 240 of a variety of lengths and diameters may be attached to the connecting shaft 202. Targeted through the alignment holes of the first and second arms 204 and 206 of the targeting assembly 201, bone screws (not shown) may be inserted through the various screw holes of the nail 240, thereby locking the nail 240 to the anatomy of a patient. In an ankle arthrodesis procedure, there are typically several screws that are inserted into the related bones (in this case the tibia, talus, and calcaneus) and these screws are sometimes placed in a medial-lateral (M/L) or anterior-posterior (A/P) direction. This variation of M/L and A/P screw placements may have as much to do with anatomy as it does with surgeon preference, and the targeting assembly 201 of the nail system 200 may allow the surgeon to pick the best and most suited option based on the patient and surgical preferences. In an embodiment, tibial screws, the talar screw, and the upper calcaneal screw may be implanted in an M/L configuration thru the nail 240. In another embodiment, surgeons may be approaching in a lateral-medial (L/M) configuration.

Conventional targeting assemblies may include targeting arms that rotate about the nail to accommodate either an M/L or A/P placement of screws. But a problem associated with conventional targeting assemblies is that when the arm is rotated, there is a risk that the alignment of the targeting arm holes to the holes in the nail is compromised. This is a particular concern for the most proximal holes on the targeting arm and the nail as they are typically the furthest away a point of rotation and are therefore usually the most affected by a magnified misalignment. In this respect, advantages of the targeting assembly 201 may include stability provided by the first arm 204 and the connecting shaft 202 being rotationally fixed relative to each other. As such, alignment holes 218, which may be the most proximal alignment holes of the targeting assembly 201, are rotationally fix relative to the nail 240, thereby reducing or eliminating the risk of misalignment due the rotation of the first arm 204 and resulting in high targeting accuracy. The second arm 206 may be allowed to rotate around the nail 240 to accommodate various screw options as discussed in the present disclosure, including the distal screws around the joint (e.g., talar, M/L calcaneal, and A/P calcaneal). Because the holes 220 of the second arm 206 are closer to the point of rotation of the second arm 206, they are less susceptible to the targeting inaccuracies due to rotation than the holes 218 of the first arm 204 would be.

Similar to the targeting assembly 100, the targeting assembly 201 may include an angular adjustment mechanism 234 operable to secure an oblique aiming guide (not shown) along an oblique axis (not shown) that is offset from the longitudinal axis 208. In some embodiments, screws (not shown) may be inserted posterior-anterior (P/A) from the back of the calcaneus upwards toward the talus. One reason to do so is to offer additional fixation and compression across this joint, but a difficulty in inserting fixation screws in this manner may be the targeting. After the nail and associated screws have been inserted, there is only a small amount of "free space" left to utilize such screws. It is desirable to avoid drilling into existing metal such as the existing nail 240 and associated screws (not shown). In this respect, the angular adjustment mechanism 234 is operable to target a screw along an oblique axis offset from the longitudinal axis 208, thereby avoiding targeting nail 240 and instead targeting either side of the nail 240.

Figure 7A:
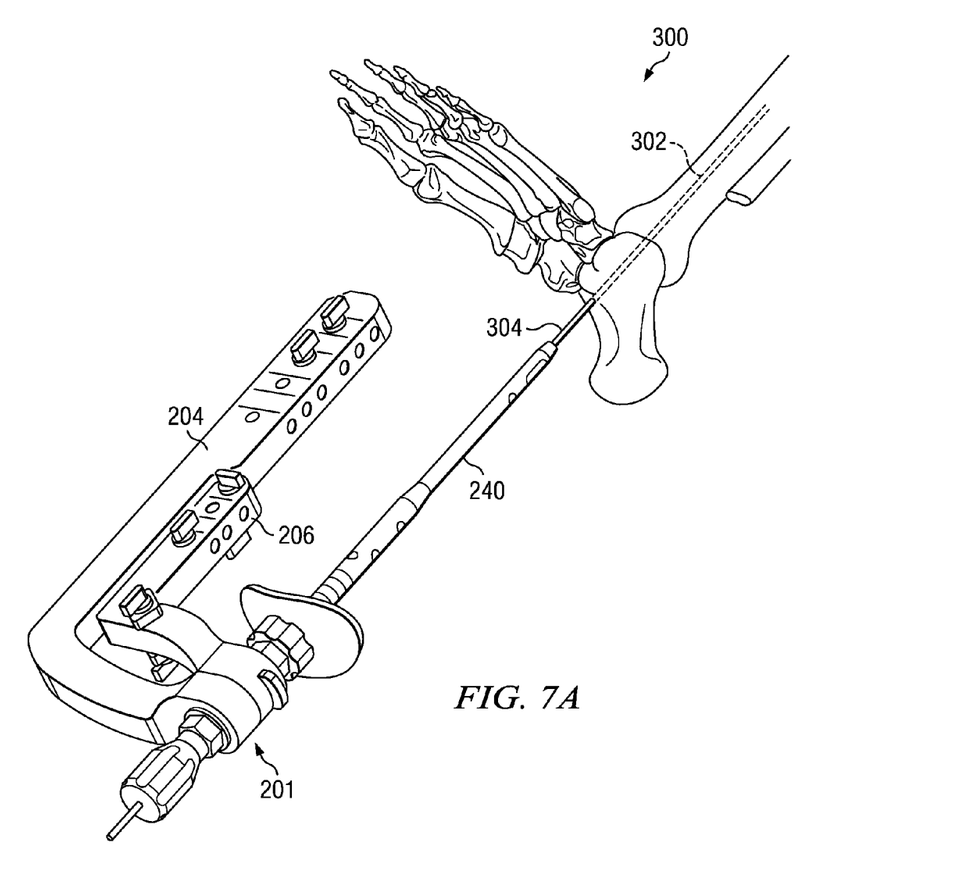
FIG. 7A is a schematic illustration of using the compression system in FIG. 5 to insert a nail into an ankle.

An exemplary embodiment of using the nail compression system 200 will be discussed with reference to FIGS. 7A-F. Shown in FIG. 7A is a patient's ankle, which has been surgically prepared to include an aperture 302 defined through the calcaneus, talus, and tibia for receiving the nail 240. In the embodiment illustrated in FIG. 7A, the nail 240 is attached to the targeting assembly 201, with both the first and second arms 204 and 206 aligned in the same plane. The nail 240 may be inserted into the aperture 302 by passing the nail 240 through a guide wire 304 disposed through a longitudinal aperture (shown in FIG. 6) of the connector shaft 202. In an embodiment, the first and second arms 204 and 206 may be angularly displaced from each other as the nail 240 is inserted (not shown). In an embodiment, the nail 240 may be inserted without the help of the guide wire 304.

Figure 7B:
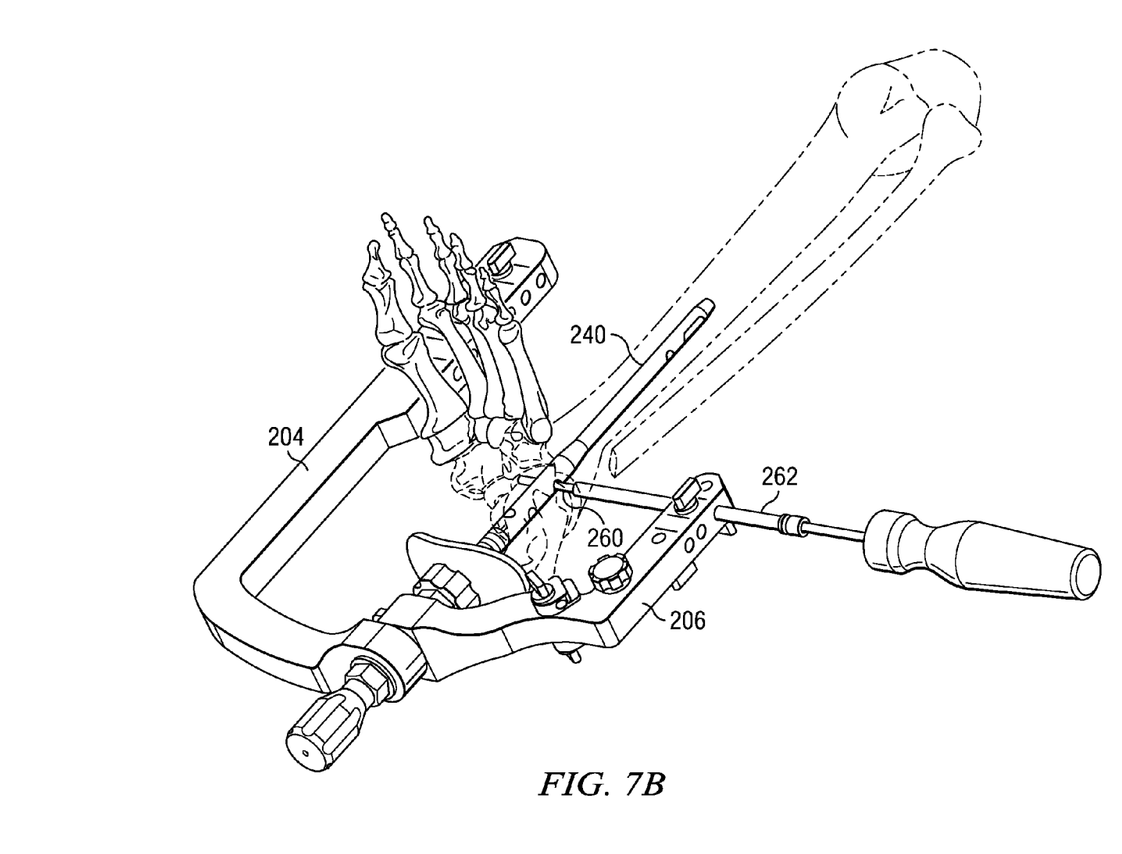
FIG. 7B is a schematic illustration of using the compression system in FIG. 5 to insert a screw into a talus bone.

After the nail 240 is inserted, the first arm 204 may be positioned for an M/L approach for the tibia screws (not shown), and the second arm 206 may be rotated to a first rotational position for an L/M approach for a talar screw 260, as shown in FIG. 7B. In another embodiment, the first arm 204 may be positioned for an L/M approach, and the second arm 206 may be rotated to a rotational position for an M/L approach. With the second arm 206 in the desired rotational position, a screw guide 262 may cooperate with the second arm 206 to target and insert the talar screw 260 through a corresponding screw hole in the nail 240 and into the talus. Once the talar screw 260 is inserted, the orientation and depth of the nail 240 relative to the anatomy of the patent are established.

Figure 7C:
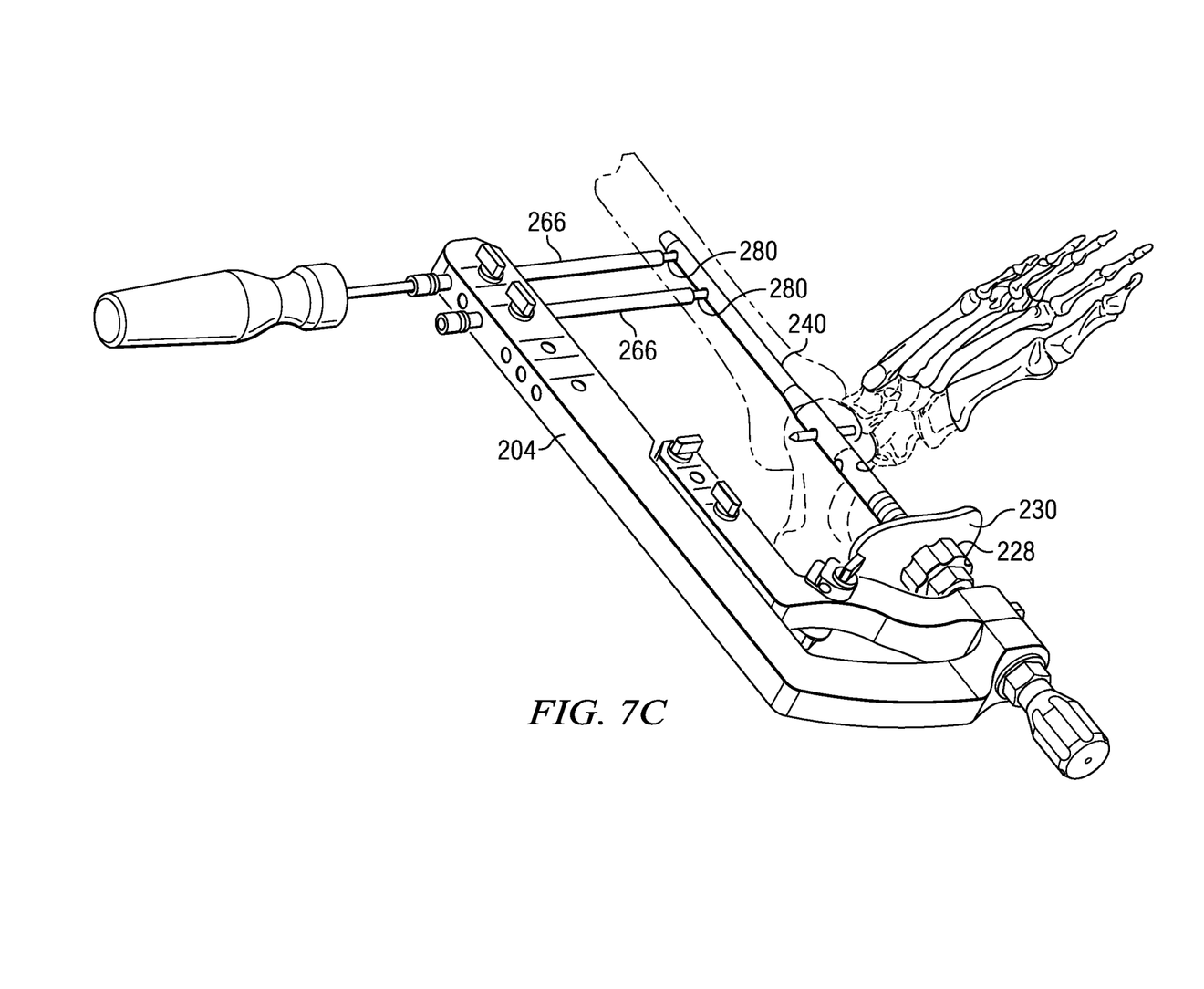
FIG. 7C is a schematic illustration of using the compression system in FIG. 5 to insert a screw into a tibia bone.

Turning to FIG. 7C, in the illustrated embodiment, two screw guides 266 may cooperate with the first arm 204 to target and insert tibial screws 280 through corresponding screw holes in the nail 240 and into the tibia. As discussed above, the tibial screws 280 may be implanted in an M/L approach as shown in FIG. 7C or in an L/m approach. After the insertion of the tibial screws 280, internal compression of the tibio-talar joint may be effected by activating a suitable internal mechanism (not shown) of the nail 240. A variety of internal mechanisms may be used for effecting internal compression in the compression nail system 200. These internal mechanisms are well-known in the art and thus would be described here. After the desired internal compression is effected, external compression of the subtalar joint may be effected by adjusting the compression element 228 to advance the cup 230 in a proximal direction until the desired compression is achieved.

Figure 7D:
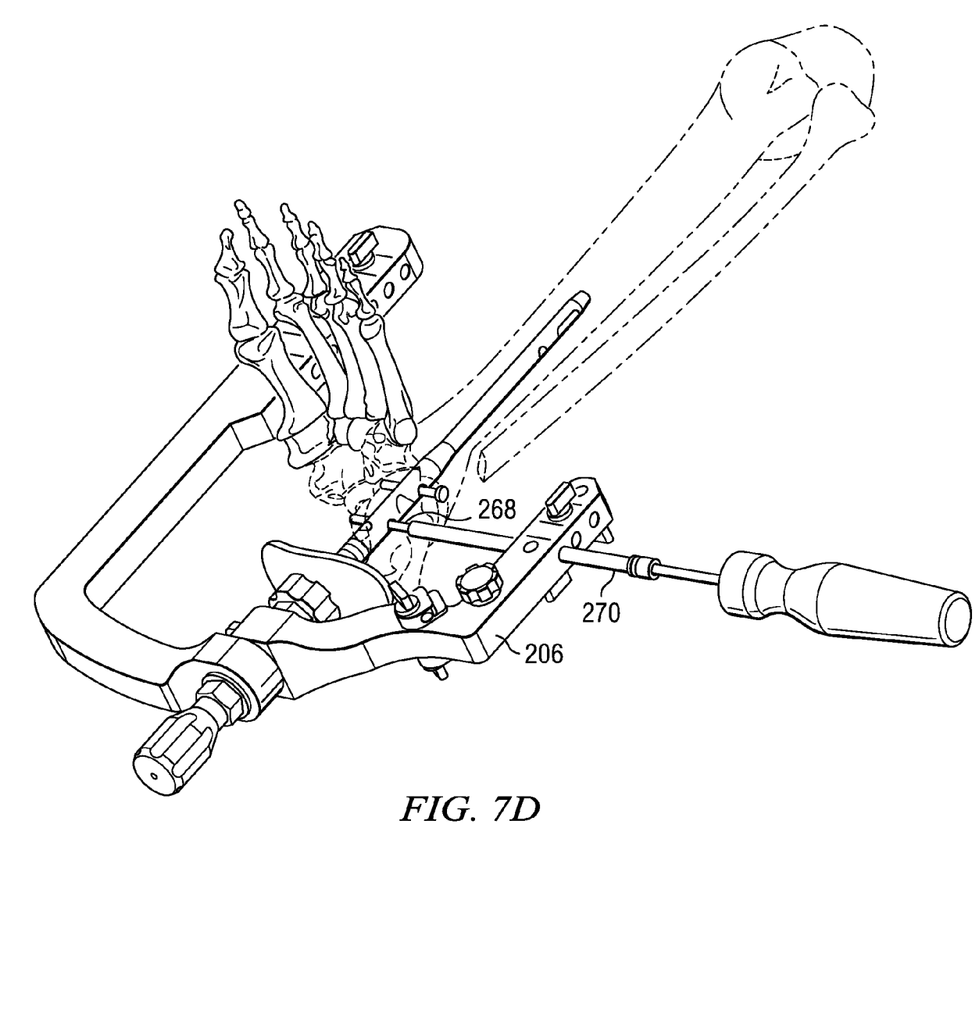
FIG. 7D is a schematic illustration of using the compression system in FIG. 5 to insert a screw into a calcaneus bone in a lateral to medial direction.
Figure 7E:
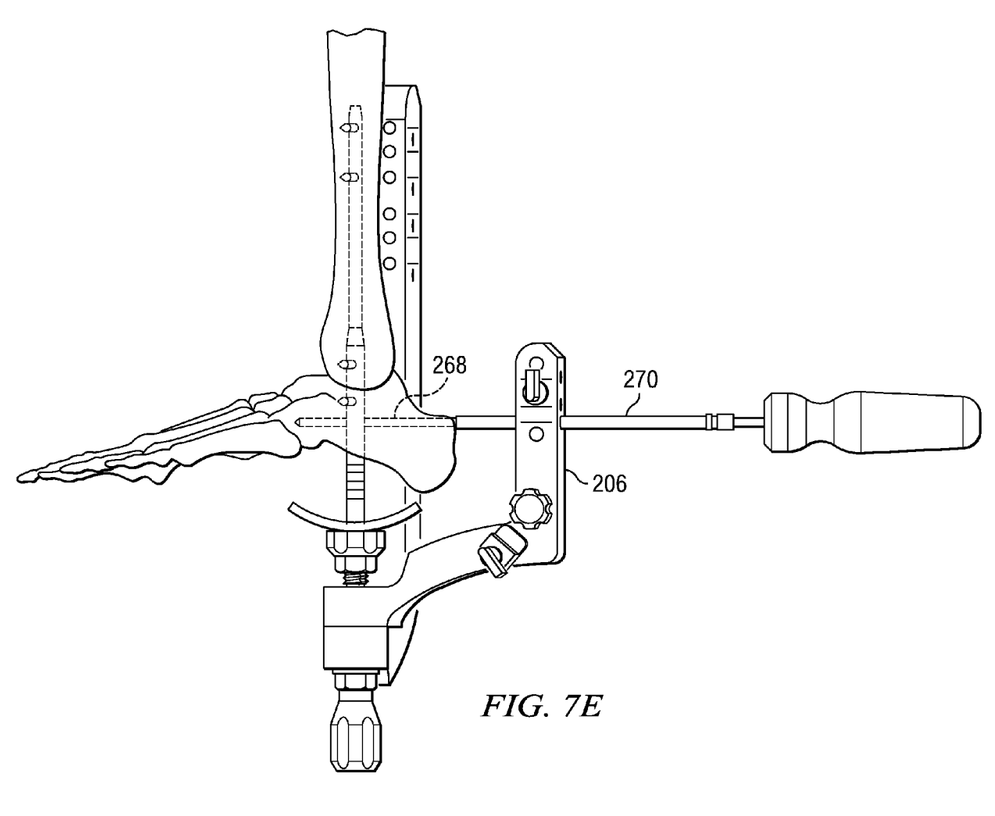
FIG. 7E is a schematic illustration of using the compression system in FIG. 5 to insert a screw into a calcaneus bone in a posterior to anterior direction.

Turning to FIGS. 7D and 7E, the second arm 206 may be rotated to the desired rotational positions to allow the insertion of two calcaneal screws 268 after the internal and external compressions have been achieved. In the illustrated embodiment, the second arm 206 is rotated to the first rotational position as shown in FIG. 7D for the insertion of a first calcaneal screw 268 in a L/M approach, and then the second arm 206 is rotated to a second rotation position as shown in FIG. 7E for the insertion of a second calcaneal screw 268 in a P/A approach. The targeting and insertion of the calcaneal screws 268 may be accomplished with the guiding of a screw guide 270. It is to be appreciated in other embodiments, the order of the insertion of the first and second calcaneal screws 268 may be varied and the approach of the insertion may be varied.

Figure 7F:
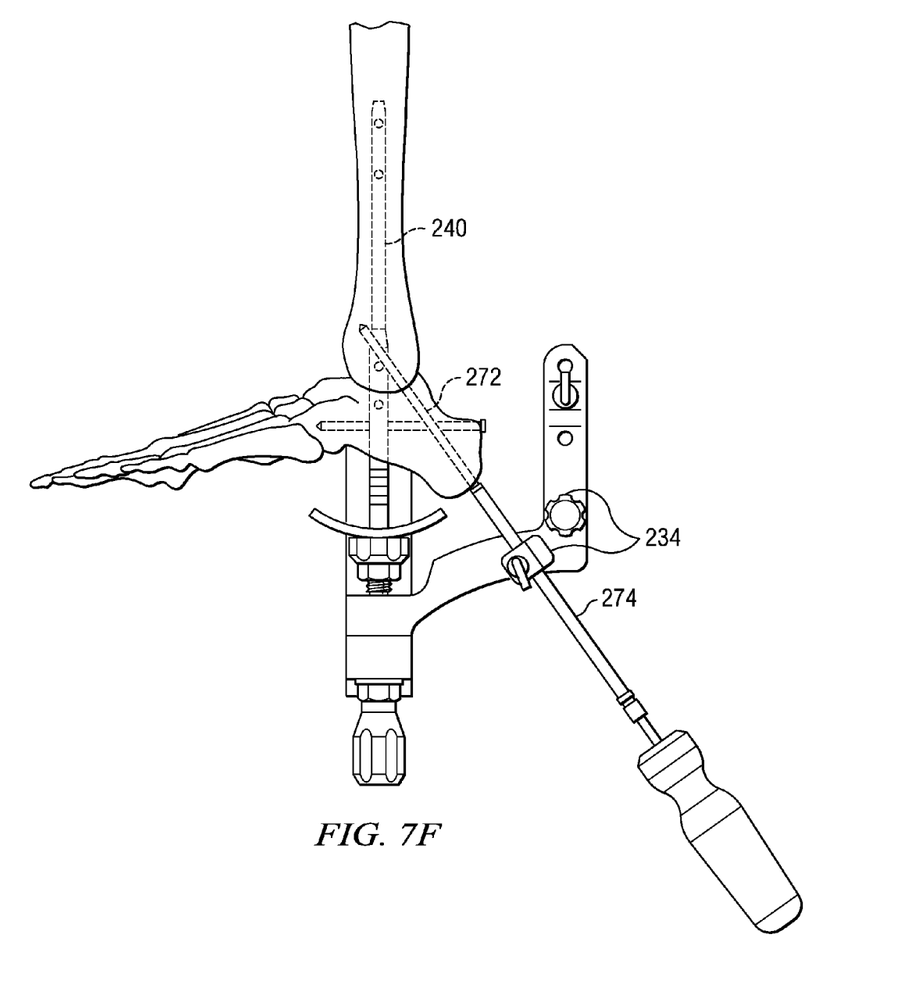
FIG. 7F is a schematic illustration of using the compression system in FIG. 5 to insert a tibio-talar compression screw in an oblique direction.

Turning to FIG. 7F, an oblique screw 272 may be implanted to obtain increased rigidity of the construct and to maintain compression before release of the external compression. As discussed above, an oblique aiming guide 274 coupled to the angular adjustment mechanism 234 may be used to target and insert the oblique screw 272 along an oblique axis (not shown) offset from the longitudinal axis 208 (not shown), thereby avoiding targeting nail 240 and instead targeting either side of the nail 240. In an embodiment, the angular adjustment mechanism 234 may include a guide knob operable to adjust the angular orientation of the oblique aiming guide 274.

While various embodiments in accordance with the principles disclosed herein have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

It will be understood that the principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A targeting assembly comprising:
   a connecting shaft defining a longitudinal axis between proximal and distal ends, wherein the proximal end includes a proximal portion and the distal end includes a distal circumferential surface, the connecting shaft comprising a plurality of recessed areas defined in the distal circumferential surface of the connecting shaft and spaced apart circumferentially by predetermined angular displacements;
   a first arm having a proximal portion and a distal base portion, the distal base portion of the first arm being connected to the distal end of the connecting shaft and the proximal portion of the first arm extends alongside the connecting shaft;
   a second arm having a proximal portion and a distal base portion, the distal base portion of the second arm being rotatably coupled to the distal end of the connecting shaft, and the proximal portion of the second arm extends alongside the connecting shaft and being operable to rotate about the longitudinal axis of the connecting shaft and relative to the first arm when being rotatably coupled to the distal end of the connecting shaft; and
   a latch extending from the distal base portion of the second arm and operable to be received in one of the plurality of recessed areas defined in the distal circumferential surface of the connecting shaft for releasably and rotatably coupling the second arm to the distal end of the connecting shaft;
   wherein the distal base portion of the first arm is connected to the distal end of the connecting shaft proximate to the distal base portion of the second arm when rotatably coupled to the distal end of the connecting shaft;
   wherein the connecting shaft and the second arm are releasably coupled by the latch and the second arm is operable to rotate and lock about the longitudinal axis of the connecting shaft and relative to the first arm in increments substantially equal to the predetermined angular displacements; and
   wherein the first arm comprises at least one alignment hole defined through the proximal portion of the first arm, the second arm comprises at least one alignment hole defined through the proximal portion of the second arm, and the connecting shaft comprises a plurality of screw holes defined through the proximal portion of the connecting shaft; and
   wherein the at least one alignment holes of the first and second arms are operable to align with the plurality of screw holes defined through the proximal portion of the connecting shaft.

2. The targeting assembly of claim 1, wherein the second arm is operable to rotate about the longitudinal axis in increments of 90 degrees.

3. The targeting assembly of claim 1, wherein the second arm is operable to rotate about the longitudinal axis in increments of 45 degrees.

4. The targeting assembly of claim 1, wherein the second arm is operable to rotate about the longitudinal axis in increments of 30 degrees.

5. The targeting assembly of claim 1, wherein the connecting shaft and the first arm are releasably coupled to one another.

6. The targeting assembly of claim 1, wherein the connecting shaft and the first arm are integrally formed.

7. The targeting assembly of claim 1, further comprising a compression element and a cup adjacent to the compression element, wherein the compression element is threadably coupled to the connecting shaft, and the connecting shaft is disposed through a central opening of the cup, and wherein a rotation of the compression element is operable to translate the cup along the longitudinal axis.

8. The targeting assembly of claim 1, wherein the second arm comprises an angular adjustment mechanism operable to receive an oblique aiming guide, the angular adjustment mechanism operable to orient the oblique aiming guide along an oblique axis that is offset from the longitudinal axis of the connecting shaft.

9. The targeting assembly of claim 1, wherein a distance between the at least one alignment hole of the first arm and the base portion of the first arm is greater than a distance between the at least one alignment hole of the second arm and the base portion of the second arm.

10. The targeting assembly of claim 1, wherein the first arm and the connecting shaft are rotationally fixed relative to each other.

11. The targeting assembly of claim 1, wherein the first arm and the connecting shaft are rotatably coupled to one another.

12. The targeting assembly of claim 1, wherein the proximal portion of the connecting shaft is a nail operable to be seated on the distal portion of the connecting shaft, wherein the nail is aligned substantially along the longitudinal axis of the connecting shaft.

13. The targeting assembly of claim 12, wherein the nail comprises the plurality of screw holes defined therethrough, and further wherein a first screw hole is in lateral alignment with a first alignment hole defined through the proximal portion of the second arm when the second arm is in a first rotational position, and a second screw hole is in lateral alignment with a second alignment hole defined through the proximal portion of the second arm when the second arm is in a second rotational position.

14. The targeting assembly of claim 13, wherein the first and second screw holes each define a lateral axis orthogonal to the longitudinal axis of the connecting shaft.

15. The targeting assembly of claim 12, wherein the nail is operable to be seated on the distal portion of the connecting shaft such that a longitudinal aperture of the connecting shaft meets an internal aperture of the nail, whereby the internal aperture of the nail is accessible from the exterior of the targeting assembly through the longitudinal aperture of the connecting shaft.

* * * * *